(12) United States Patent
Rubner et al.

(10) Patent No.: US 8,637,071 B2
(45) Date of Patent: *Jan. 28, 2014

(54) METHOD FOR MAKING MEDICAL DEVICES HAVING ANTIMICROBIAL COATINGS THEREON

(71) Applicant: Novartis AG, Basel (CH)

(72) Inventors: Michael F. Rubner, Westford, MA (US); Sung Yun Yang, Cambridge, MA (US); Yongxing Qiu, Duluth, GA (US); Lynn Cook Winterton, Keller, TX (US); John Martin Lally, Benbrook, TX (US)

(73) Assignee: Novartis AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 13/648,379

(22) Filed: Oct. 10, 2012

(65) Prior Publication Data

US 2013/0034593 A1   Feb. 7, 2013

Related U.S. Application Data

(62) Division of application No. 10/732,543, filed on Dec. 10, 2003, now Pat. No. 8,309,117.

(60) Provisional application No. 60/435,003, filed on Dec. 19, 2002.

(51) Int. Cl.
*A61K 9/00* (2006.01)
*A61K 9/70* (2006.01)

(52) U.S. Cl.
USPC ............ 424/429; 264/2.6; 424/618; 514/839; 977/777

(58) Field of Classification Search
None
See application file for complete search history.

(56) References Cited

U.S. PATENT DOCUMENTS

| | | |
|---|---|---|
| 4,849,223 A | 7/1989 | Pratt |
| 5,213,801 A | 5/1993 | Sakuma |
| 5,681,575 A | 10/1997 | Burrell |
| 5,783,454 A | 7/1998 | Spallholz |
| 5,897,673 A | 4/1999 | Nishida |
| 5,994,151 A | 11/1999 | Spallholz |
| 6,033,917 A | 3/2000 | Spallholz |
| 6,040,197 A | 3/2000 | Spallholz |
| 6,043,098 A | 3/2000 | Spallholz |
| 6,043,099 A | 3/2000 | Spallholz |
| 6,077,714 A | 6/2000 | Spallholz |
| 6,420,349 B1 | 7/2002 | Snyder |
| 6,451,871 B1 | 9/2002 | Winterton |
| 6,465,456 B2 | 10/2002 | Springer |
| 6,719,929 B2 | 4/2004 | Winterton |
| 6,843,784 B2 | 1/2005 | Modak |
| 7,297,725 B2 | 11/2007 | Winterton |
| 7,566,746 B2 | 7/2009 | Winterton |
| 7,705,067 B2 | 4/2010 | Winterton |
| 2001/0045676 A1 | 11/2001 | Winterton |
| 2001/0055622 A1 | 12/2001 | Burrell |
| 2002/0035264 A1 | 3/2002 | Kararli |
| 2002/0094984 A1 | 7/2002 | Snyder |
| 2002/0194958 A1 | 12/2002 | Lee |
| 2003/0065051 A1 | 4/2003 | Winterton |
| 2005/0008676 A1 | 1/2005 | Qiu |
| 2005/0058844 A1 | 3/2005 | Rubner |
| 2008/0129956 A1 | 6/2008 | Winterton |
| 2009/0288369 A1 | 11/2009 | Winterton |

FOREIGN PATENT DOCUMENTS

| | | |
|---|---|---|
| JP | 6293611 A2 | 10/1994 |
| JP | 8151310 A2 | 6/1996 |
| JP | 9228241 A2 | 9/1997 |
| KR | 2004089035 | 10/2004 |
| WO | 99-35520 | 7/1999 |
| WO | 01-57118 | 8/2001 |
| WO | 01-68090 | 9/2001 |
| WO | 01-68091 | 9/2001 |
| WO | 01-76594 | 10/2001 |
| WO | 01-92924 | 12/2001 |
| WO | 02-49683 | 6/2002 |
| WO | 02064183 | 8/2002 |
| WO | 02-085385 | 10/2002 |
| WO | 02-097481 | 10/2002 |
| WO | 02085387 | 10/2002 |

OTHER PUBLICATIONS

Machine Translation of JP 09-228241 (1997).
Machine Translation of JP 06-293611 (1994).
Japan Office Action Notification of Reasons for Rejection; Dispatch No. 499664, Dispatch Date: Jul. 13, 2010, Japanese Patent Application No. 2004-561356.
Japan Office Action Notification of Reasons for Rejection; Dispatch No. 499664, Dispatch Date: Jul. 13, 2010, Japanese Patent Application No. 2004-561354.
Mecking, Thomann, Frey and Sunder: "Preparaton of Catalytically Active Palladium Nanoclusters in Compartments of Amphiphillic Hyperbranched Polyglycerols", Feb. 17, 2000, pp. 3958-3960.
Siderov, Bronstein, Valetsky, Hartmann, Colfen, Schnablegger and Antoinetti,"Stabilization of Metal nanoparticles in Aqueous Medium by Polyethyleneoxide-Polyethyleneimine Block Copolymers" Nov. 30, 1998, pp. 197-211.
Meeking, Schlotterbeck, Thomann, Soddeman, Stieger, Richtering, Kautz,"Formation of metal Nanoparticles in Modified Hyperbranched Polyglycerols and use as soluble Separable Catalysts", 2001, pp. 511-512.

(Continued)

*Primary Examiner* — Daniel Sullivan
*Assistant Examiner* — Barbara Frazier
(74) *Attorney, Agent, or Firm* — Sheng-Hsin Hu; Jian Zhou

(57) ABSTRACT

The present invention provides a method for preparing a medical device, preferably a contact lens, having an antimicrobial metal-containing LbL coating on a medical device, wherein the antimicrobial metal-containing LbL coating comprises at least one layer of a negatively charged polyionic material having —COOAg groups and/or silver nanoparticles formed by reducing $Ag^+$ ions associated with the —COO⁻ groups of the negatively charged polyionic material. In addition, the present invention provides a medical device prepared according to a method of the invention.

2 Claims, No Drawings

(56) References Cited

OTHER PUBLICATIONS

Petit, Lixon, and pileni,"In Situ Synthesis of Silver Nanocluster in AOT Reverse Micelles", 1993, pp. 12974-12983.

Aymonier, Schlotterbeck, Antoinietti, Zacharias, Thomann, Tiller and Mecking, "Hybrids of Silver Nanoparticles with Amphiphillic Hyperbranched Macromolecules Exhibiting Antimicrobial Properties", 2002, pp. 3018-3019.

Trapalis, Vaimakis, Kharlamov, Kokoris and Kordas. "Nanostructured MeSiO2 (Me=Ag, Cu) Coatings with Antibacterial Activity", Aug. 4-8, 2002.

Vasylyev, Mishchuk, Omishchenko, and Gurin. "Nanostructured Transformation of the Co-Cr-Alloy Surface at Mechanical Treatment in the Medium Saliva" Aug. 4-8, 2002.

International Search Report for PCT/EP03/14531, mailed Aug. 11, 2004.

"Biomaterials by Design: Layer by Layer Assembled Ion-Selective and Biocompatible Films of TiO2 Nanoshels for Neurochemical Monitoring" Koktysh, Liang, Yun, Pastoriza-Santos, Matts, Giersig, Serra-Rodriguez, Liz-Marzan, Kotov, Advanced Functional Materials (2002) 12 (4), 255-265, Nov. 2002.

"Thin Films of Ag Nanoparticles Prepared from the Reduction of Agl Nanoparticles in Self-Assembled Films" Zhang, Junhu et al., Journal of Colloid and Interface Science (2002), 255(1), 115-118, 2002.

"Metallodielectric Photonic Structures Based on Polyelectrolyte Multi-layers" Wang, Tom C. et al., Advanced Materials (Weinheim, Germany) (2002), 14(21), 1534-1537, 2002.

Evaluation of "Bacteriostatic" contact Lenses, Thomas Chalkley, et al, pp. 866-869.

Antimicrobial Efficacy of a Silver Layer on Hydrogel Lenses, S. Nissen, et al, Ophthalmologe, 7:640-643, 2000 (abstract).

Silver-Based Crystalline Nanoparticles, Microbially Fabricated, Tanja Klaus, et al PNAS, Nov. 23, 1999, vol. 96, No. 24, pp. 13611-13614.

Hydogenous and Exogenous Ocular and Systemic Silver Deposition, W. H. Spencer, et al.,Society UK 1980, 100,171.

Formulation and Stabilization of Silver Nanoparticles through Reduction by N, N.-Dimethylformamide, Isabel Pastoriza-Santos, et al., 1999 American Chemical Society, Jan. 15, 1999, pp. 948-951.

METHOD FOR MAKING MEDICAL DEVICES HAVING ANTIMICROBIAL COATINGS THEREON

This application is a division of U.S. patent application Ser. No. 10/732,543, filed Dec. 10, 2003, which claims under under 35 USC §119(e) the benefit of the filing date of U.S. provisional application Ser. No. 60/435,003 filed Dec. 19, 2002, incorporated herein by reference in its entirety.

The present invention generally relates to a medical device having an antimicrobial metal-containing layer-by-layer coating thereon and to a method for making the medical device of the invention.

BACKGROUND

Contact lenses are often exposed to one or more microorganisms during wear, storage and handling. They can provide surfaces onto which the microorganisms can adhere and then proliferate to form a colony. Microbial adherence to and colonization of contact lenses may enable microorganisms to proliferate and to be retained at the ocular surface for prolonged periods and thereby may cause infection or other deleterious effects on the ocular health of the eye in which the lens is used. Therefore, it is desirous to make various efforts to minimize and/or eliminate the potential for microorganism adhesion to and colonization of contact lenses.

Many attempts have been made to develop antimicrobial medical devices. Two approaches have been proposed. One approach is to incorporate antimicrobial compounds into a polymeric composition for molding a contact lens. For example, Chalkley et al. in Am. J. Ophthalmology 1966, 61:866-869, disclosed that germicidal agents were incorporated into contact lenses. U.S. Pat. No. 4,472,327 discloses that antimicrobial agents may be added to the monomer before polymerization and locked into the polymeric structure of the lens. U.S. Pat. Nos. 5,358,688 and 5,536,861 disclose that contact lenses having antimicrobial properties may be made from quaternary ammonium group containing organosilicone polymers. European patent application EP0604369 discloses that deposit-resistant contact lenses can be prepared from hydrophilic copolymers that are based on 2-hydroxyethyl methacrylate and comonomers containing a quaternary ammonium moiety. Another example is an ocular lens material, disclosed in European patent application EP0947856A2, which comprises a quaternary phosphonium group-containing polymer. A further example is U.S. Pat. No. 5,515,117 which discloses contact lenses and contact lens cases made from materials which comprise polymeric materials and effective antimicrobial components. A still further example is U.S. Pat. No. 5,213,801 which discloses contact lenses made from materials comprising a hydrogel and an antimicrobial ceramic containing at least one metal selected from Ag, Cu and Zn. There are some disadvantages associated with this approach for making antimicrobial contact lenses. Polymeric compositions having antimicrobial properties may not possess all properties desired for contact lenses, especially extended-wear contact lenses, which hinders their practice uses.

The other approach for making antimicrobial medical devices is to form antimicrobial coatings, containing leachable or covalently attached antimicrobial agents, on medical devices. Antimicrobial coatings containing leachable antimicrobial agents may not be able to provide antimicrobial activity over the period of time when used in the area of the human body. In contrast, antimicrobial coating containing covalently bound antimicrobial agents can provide antimicrobial activity over a relatively longer period of time. However, antimicrobial compounds in such coatings may exhibit diminished activity when comparing the activity of the unbound corresponding antimicrobial compounds in solution, unless assisted by hydrolytic breakdown of either the bound antimicrobial compounds or the coating itself. Like the above-described approach, the antimicrobial coating may not be able to provide desired surface properties such as hydrophilicity and/or lubricity and also may have adverse effects on the desired bulk properties of a medical device (for example, the oxygen permeability of a contact lens).

Currently, a wide variety of antimicrobial agents have been proposed to be used as coatings for contact lenses (see, for example, U.S. Pat. No. 5,328,954). Prior known antimicrobial coatings include antibiotics, lactoferrin, metal chelating agents, substituted and unsubstituted polyhydric phenols, amino phenols, alcohols, acid and amine derivatives, and quaternary ammonium group-containing compounds. However, such antimicrobial coatings have disadvantages and are unsatisfactory. The overuse of antibiotics can lead to proliferation of antibiotic-resistant microorganisms. Other coatings may not have broad spectrum antimicrobial activity, may produce ocular toxicity or allergic reactions, or may adversely affect lens properties required for ensuring corneal health and for providing the patient with good vision and comfort.

Therefore, there is a need for antimicrobial coatings that can provide high bactericidal efficacy and broad spectrum antimicrobial activity coupled with low cytotoxicity. There is also a need for new contact lenses having antimicrobial coatings, which have high bactericidal efficacy, a broad spectrum of antimicrobial activities, and minimal adverse effects on the wearer's ocular health and comfort. Such contact lenses may have increased safety as extended-wear contact lenses which could provide comfort, convenience, and safety.

Moreover, surgical and device related infection remains to be one of the main clinical and economic challenges in the field of medical devices and in health care industry in general. Each year, as many as 2 million hospital patients in the United States develop nosocomial infections, and approximately 80% of the 80,000 annual deaths due to nosocomial infections are device-related. A potent and cost-effective antimicrobial coating for medical devices would be a key to mitigate the infection-related clinical challenges and economic burden of health care.

One object of the invention is to provide an antimicrobial coating which has a high antimicrobial efficacy coupled with low cytotoxicity.

Another object of the invention is to provide a medical device having an antimicrobial coating that has a high antimicrobial efficacy coupled with low cytotoxicity.

A further object of the invention is to provide a cost-effective and efficient process for forming an antimicrobial coating on a medical device.

SUMMARY OF THE INVENTION

These and other objects of the invention are met by the various aspects of the invention described herein.

The invention, in one aspect, provides a method for forming a silver nanoparticle-containing antimicrobial LbL coating on a medical device. The method comprises: obtaining a medical device with a polyelectrolyte LbL coating thereon, wherein the polyelectrolyte LbL coating includes one or more bilayers of a negatively charged polyionic material having —COOH groups and a positively charged polyionic material; immersing the medical device having the polyelectrolyte LbL coating in a solution containing silver ions for a period of time sufficient to replace a desired amount of $H^+$ with silver ions; and reducing silver ions contained in the polyelectrolyte LbL coating to form silver nano-particles.

The invention, in another aspect, provides a method for forming an antimicrobial metal-containing LbL coating on a medical device. The method comprises alternatively applying, in no particular order, at least one layer of a negatively charged polyionic material having —COOAg groups and at least one layer of a positively charged polyionic material onto a medical device to form the antimicrobial metal-containing LbL coating.

The invention, in a further aspect, provides a medical device having a core material and an antimicrobial metal-containing layer-by-layer (LbL) coating that is not covalently attached to the medical device and can impart to the medical device an increased hydrophilicity, wherein the antimicrobial metal-containing LbL coating comprises at least one layer of a negatively charged polyionic material having —COOAg groups and/or silver nanoparticles formed by reducing $Ag^+$ ions associated with the —COO$^-$ groups of the negatively charged polyionic material.

These and other aspects of the invention will become apparent from the following description of the presently preferred embodiments. The detailed description is merely illustrative of the invention and does not limit the scope of the invention, which is defined by the appended claims and equivalents thereof. As would be obvious to one skilled in the art, many variations and modifications of the invention may be effected without departing from the spirit and scope of the novel concepts of the disclosure.

DETAILED DESCRIPTION OF THE PREFERRED EMBODIMENTS

Unless defined otherwise, all technical and scientific terms used herein have the same meaning as commonly understood by one of ordinary skill in the art to which this invention belongs. Generally, the nomenclature used herein and the laboratory procedures are well known and commonly employed in the art. Conventional methods are used for these procedures, such as those provided in the art and various general references. Where a term is provided in the singular, the inventors also contemplate the plural of that term. The nomenclature used herein and the laboratory procedures described below are those well known and commonly employed in the art. As employed throughout the disclosure, the following terms, unless otherwise indicated, shall be understood to have the following meanings.

An "article" refers to an ophthalmic lens, a mold for making an ophthalmic lens, or a medical device other than ophthalmic lens.

A "medical device", as used herein, refers to a device or a part thereof having one or more surfaces that contact tissue, blood, or other bodily fluids of patients in the course of their operation or utility. Exemplary medical devices include: (1) extracorporeal devices for use in surgery such as blood oxygenators, blood pumps, blood sensors, tubing used to carry blood and the like which contact blood which is then returned to the patient; (2) prostheses implanted in a human or animal body such as vascular grafts, stents, pacemaker leads, heart valves, and the like that are implanted in blood vessels or in the heart; (3) devices for temporary intravascular use such as catheters, guide wires, and the like which are placed into blood vessels or the heart for purposes of monitoring or repair; (4) artificial tissues such as artificial skin for burn patients; (5) dentifices, dental moldings; (6) ophthalmic devices; and (7) cases or containers for storing ophthalmic devices or ophthalmic solutions.

An "ophthalmic device", as used herein, refers to a contact lens (hard or soft), an intraocular lens, a corneal onlay, other ophthalmic devices (e.g., stents, glaucoma shunt, or the like) used on or about the eye or ocular vicinity.

"Biocompatible", as used herein, refers to a material or surface of a material, which may be in intimate contact with tissue, blood, or other bodily fluids of a patient for an extended period of time without significantly damaging the ocular environment and without significant user discomfort.

"Ophthalmically compatible", as used herein, refers to a material or surface of a material which may be in intimate contact with the ocular environment for an extended period of time without significantly damaging the ocular environment and without significant user discomfort. Thus, an ophthalmically compatible contact lens will not produce significant corneal swelling, will adequately move on the eye with blinking to promote adequate tear exchange, will not have substantial amounts of protein or lipid adsorption, and will not cause substantial wearer discomfort during the prescribed period of wear.

"Ocular environment", as used herein, refers to ocular fluids (e.g., tear fluid) and ocular tissue (e.g., the cornea) which may come into intimate contact with a contact lens used for vision correction, drug delivery, wound healing, eye color modification, or other ophthalmic applications.

A "monomer" means a low molecular weight compound that can be polymerized. Low molecular weight typically means average molecular weights less than 700 Daltons.

A "macromer" refers to medium and high molecular weight compounds or polymers that contain functional groups capable of further polymerization. Medium and high molecular weight typically means average molecular weights greater than 700 Daltons.

"Polymer" means a material formed by polymerizing one or more monomers.

"Surface modification", as used herein, means that an article has been treated in a surface treatment process (or a surface modification process), in which, by means of contact with a vapor or liquid, and/or by means of application of an energy source (1) a coating is applied to the surface of an article, (2) chemical species are adsorbed onto the surface of an article, (3) the chemical nature (e.g., electrostatic charge) of chemical groups on the surface of an article are altered, or (4) the surface properties of an article are otherwise modified.

"LbL coating", as used herein, refers to a coating that is not covalently attached to an article, preferably a medical device, and is obtained through a layer-by-layer ("LbL") deposition of polyionic or charged materials on an article.

The term "bilayer" is employed herein in a broad sense and is intended to encompass: a coating structure formed on a medical device by alternatively applying, in no particular order, one layer of a first polyionic material (or charged material) and subsequently one layer of a second polyionic material (or charged material) having charges opposite of the charges of the first polyionic material (or the charged material); or a coating structure formed on a medical device by alternatively applying, in no particular order, one layer of a first charged polymeric material and one layer of a non-charged polymeric material or a second charged polymeric material. It should be understood that the layers of the first and second coating materials (described above) may be intertwined with each other in the bilayer.

A medical device having a core material and an LbL coating, which comprises at least one layer of a charged polymeric material and one layer of a non-charged polymeric material that can be non-covalently bonded to the charged polymeric material, can be prepared according to a method disclosed in a co-pending U.S. patent application Ser. No. 10/654,566 filed Sep. 3, 2003, herein incorporated by reference in its entirety.

As used herein, "asymmetrical coatings" on an ophthalmic lens refers to the different coatings on the first surface and the opposite second surface of the ophthalmic lens. As used herein, "different coatings" refers to two coatings that have different surface properties or functionalities.

A "capping layer", as used herein, refers to the last layer of a coating material which is applied onto the surface of a medical device.

A "capping bilayer", as used herein, refers to the last bilayer of a first coating material and a second coating material, which is applied onto the surface of a medical device.

A "polyquat", as used herein, refers to a polymeric quaternary ammonium group-containing compound.

As used herein, a "polyionic material" refers to a polymeric material that has a plurality of charged groups, such as polyelectrolytes, p- and n-type doped conducting polymers. Polyionic materials include both polycationic (having positive charges) and polyanionic (having negative charges) materials.

An "antimicrobial LbL coating", as used herein, refers to an LbL coating that imparts to a medical device the ability to decrease or eliminate or inhibit the growth of microorganisms on the surface of the medical device or in an adjacent area extending from the medical device. An antimicrobial LbL coating on a medical device of the invention exhibit preferably at least a 1-log reduction (≥90% inhibition), more preferably at least a 2-log reduction (≥99% inhibition), of viable microorganisms.

An "antimicrobial agent", as used herein, refers to a chemical that is capable of decreasing or eliminating or inhibiting the growth of microorganisms such as that term is known in the art.

"Antimicrobial metals" are metals whose ions have an antimicrobial effect and which are biocompatible. Preferred antimicrobial metals include Ag, Au, Pt, Pd, Ir, Sn, Cu, Sb, Bi and Zn, with Ag being most preferred.

"Antimicrobial metal-containing nanoparticles" refers to particles having a size of less than 1 micrometer and containing at least one antimicrobial metal present in one or more of its oxidation states. For example, silver-containing nanoparticles can contain silver in one or more of its oxidation states, such as $Ag^0$, $Ag^{1+}$, and $Ag^{2+}$.

"Antimicrobial metal nanoparticles" refers to particles which is made of one or more antimicrobial metals and have a size of less than 1 micrometer. The antimicrobial metals in the antimicrobial metal nanoparticles can be present in one or more of its oxidation state.

An "averaged contact angle" refers to a contact angle (Sessile Drop), which is obtained by averaging measurements of at least 3 individual medical devices.

As used herein, "increased surface hydrophilicity" or "increased hydrophilicity" in reference to a coated medical device means that the coated medical device has a reduced averaged contact angle compared with an uncoated medical device.

The invention, in one aspect, provides a method for forming a silver nanoparticle-containing antimicrobial LbL coating on a medical device. The method comprises: obtaining a medical device with a polyelectrolyte LbL coating thereon, wherein the polyelectrolyte LbL coating includes one or more bilayers of a negatively charged polyionic material having —COOH groups and a positively charged polyionic material; immersing the medical device having the polyelectrolyte LbL coating in a solution containing silver ions for a period of time sufficient to replace a desired amount of $H^+$ with silver ions; and reducing silver ions contained in the polyelectrolyte LbL coating to form silver nano-particles.

It has been discovered here that an antimicrobial metal, silver, in particular silver nano-particles can be incorporated cost-effectively into an LbL coating according to a method of the invention. It is found that an silver nanoparticle-containing LbL coating of the invention may possess several advantages as follows. It can impart to a medical device not only an antimicrobial activity but also an increased surface hydrophilicity. It has minimal adverse effects on the desired bulk properties of, for example, a contact lens, such as oxygen permeability, ion permeability, and optical properties. An silver nanoparticle-containing LbL coating of the invention formed on a medical device can adhere well to a medical device and be stable, even after several cycles of autoclaving treatments. The process for forming a silver nanoparticle-containing LbL coating of the invention is well suited for automation and can be used to coat a wide range of substrate (polymeric, glass, quartz, ceramic, metal) and in any geometry. Out-diffusion of silver from the silver-containing coating is controllable.

In accordance with the present invention, the core material of a medical device (substrate) may be any of a wide variety of polymeric materials. Exemplary core materials include, but are not limited to, hydrogels, silicone-containing hydrogels, polymers and copolymers of styrene and substituted styrenes, ethylene, propylene, acrylates and methacrylates, N-vinyl lactams, acrylamides and methacrylamides, acrylonitrile, acrylic and methacrylic acids.

A preferred group of core materials to be coated are those being conventionally used for the manufacture of biomedical devices, e.g. contact lenses, in particular contact lenses for extended wear, which are not hydrophilic per se. Such materials are known to the skilled artisan and may comprise for example polysiloxanes, perfluoroalkyl polyethers, fluorinated poly(meth)acrylates or equivalent fluorinated polymers derived e.g. from other polymerizable carboxylic acids, polyalkyl (meth)acrylates or equivalent alkylester polymers derived from other polymerizable carboxylic acids, or fluorinated polyolefins, such as fluorinated ethylene or propylene, for example tetrafluoroethylene, preferably in combination with specific dioxols, such as perfluoro-2,2-dimethyl-1,3-dioxol. Examples of suitable bulk materials are e.g. Lotrafilcon A, Neofocon, Pasifocon, Telefocon, Silafocon, Fluorsilfocon, Paflufocon, Silafocon, Elastofilcon, Balifilcon A, Fluorofocon, or Teflon AF materials, such as Teflon AF 1600 or Teflon AF 2400 which are copolymers of about 63 to 73 mol % of perfluoro-2,2-dimethyl-1,3-dioxol and about 37 to 27 mol % of tetrafluoroethylene, or of about 80 to 90 mol % of perfluoro-2,2-dimethyl-1,3-dioxol and about 20 to 10 mol % of tetrafluoroethylene.

Another group of preferred core materials to be coated is amphiphilic-segmented copolymers comprising at least one hydrophobic segment and at least one hydrophilic segment, which are linked through a bond or a bridge member. Examples are silicone hydrogels, for example those disclosed in PCT applications WO 96/31792 to Nicolson et al. and WO 97/49740 to Hirt et al..

A particular preferred group of core materials to be coated comprises organic polymers selected from polyacrylates, polymethacrylates, polyacrylamides, poly(N,N-dimethylacrylamides), polymethacrylamides, polyvinyl acetates, polysiloxanes, perfluoroalkyl polyethers, fluorinated polyacrylates or -methacrylates and amphiphilic segmented copolymers comprising at least one hydrophobic segment, for example a polysiloxane or perfluoroalkyl polyether segment or a mixed polysiloxane/perfluoroalkyl polyether segment, and at least one hydrophilic segment, for example a polyoxazoline, poly(2-hydroxyethylmethacrylate), polyacrylamide, poly(N,N-dimethylacrylamide), polyvinylpyrrolidone polyacrylic or polymethacrylic acid segment or a copolymeric mixture of two or more of the underlying monomers.

The core material to be coated may also be any blood-contacting material conventionally used for the manufacture of renal dialysis membranes, blood storage bags, pacemaker leads or vascular grafts. For example, the material to be modified on its surface may be a polyurethane, polydimethylsiloxane, polytetrafluoroethylene, polyvinylchloride, Dacron™ or Silastic™ type polymer, or a composite made therefrom.

Moreover, the core material to be coated may also be an inorganic or metallic base material without suitable reactive groups, e.g. ceramic, quartz, or metals, such as silicon or gold, or other polymeric or non-polymeric substrates. e.g., for implantable biomedical applications, ceramics are very useful. In addition, e.g. for biosensor purposes, hydrophilically coated base materials are expected to reduce nonspecific binding effects if the structure of the coating is well controlled. Biosensors may require a specific carbohydrate coating on gold, quartz, or other non-polymeric substrates.

The core material to be coated can be subjected to a surface modification before applying an antimicrobial coating. Exemplary surface treatment processes include, but are not limited to, a surface treatment by energy (e.g., a plasma, a static electrical charge, irradiation, or other energy source), chemical treatments, the grafting of hydrophilic monomers or macromers onto the surface of an article, and layer-by-layer deposition of polyelectrolytes. A preferred class of surface treatment processes are plasma processes, in which an ionized gas is applied to the surface of an article. Plasma gases and processing conditions are described more fully in U.S. Pat. Nos. 4,312,575 and 4,632,844, which are incorporated herein by reference. The plasma gas is preferably a mixture of lower alkanes and nitrogen, oxygen or an inert gas.

The form of the core material to be coated may vary within wide limits. Examples are particles, granules, capsules, fibers, tubes, films or membranes, preferably moldings of all kinds such as ophthalmic moldings, for example intraocular lenses, artificial cornea or in particular contact lenses.

The polyionic materials that may be employed in the present invention include polyanionic and polycationic polymers. Examples of suitable polyanionic polymers include, for example, a synthetic polymer, a biopolymer or modified biopolymer comprising carboxy, sulfo, sulfato, phosphono or phosphato groups or a mixture thereof, or a salt thereof, for example, a biomedical acceptable salt and especially an ophthalmically acceptable salt thereof when the article to be coated is an ophthalmic device.

Examples of synthetic polyanionic polymers are: a linear polyacrylic acid (PAA), a branched polyacrylic acid, a polymethacrylic acid (PMA), a polyacrylic acid or polymethacrylic acid copolymer, a maleic or fumaric acid copolymer, a poly(styrenesulfonic acid) (PSS), a polyamido acid, a carboxy-terminated polymer of a diamine and a di- or polycarboxylic acid (e.g., carboxy-terminated Starburst™ PAMAM dendrimers from Aldrich), a poly(2-acrylamido-2-methylpropanesulfonic acid) (poly-(AMPS)), an alkylene polyphosphate, an alkylene polyphosphonate, a carbohydrate polyphosphate or carbohydrate polyphosphonate (e.g., a teichoic acid). Examples of a branched polyacrylic acid include a Carbophil® or Carbopol® type from Goodrich Corp. Examples of a copolymer of acrylic or methacrylic acid include a copolymerization product of an acrylic or methacrylic acid with a vinyl monomer including, for example, acrylamide, N,N-dimethyl acrylamide or N-vinylpyrrolidone.

Examples of polyanionic biopolymers or modified biopolymers are: hyaluronic acid, glycosaminoglycanes such as heparin or chondroitin sulfate, fucoidan, poly-aspartic acid, poly-glutamic acid, carboxymethyl cellulose, carboxymethyl dextrans, alginates, pectins, gellan, carboxyalkyl chitins, carboxymethyl chitosans, sulfated polysaccharides.

A preferred polyanionic polymer is a linear or branched polyacrylic acid or an acrylic acid copolymer. A more preferred anionic polymer is a linear or branched polyacrylic acid. A branched polyacrylic acid in this context is to be understood as meaning a polyacrylic acid obtainable by polymerizing acrylic acid in the presence of suitable (minor) amounts of a di- or polyvinyl compound.

A suitable polycationic polymer as part of the bilayer is, for example, a synthetic polymer, biopolymer or modified biopolymer comprising primary, secondary or tertiary amino groups or a suitable salt thereof, preferably an ophthalmically acceptable salt thereof, for example a hydrohalogenide such as a hydrochloride thereof, in the backbone or as substituents. Polycationic polymers comprising primary or secondary amino groups or a salt thereof are preferred.

Examples of synthetic polycationic polymers are:
(i) a polyallylamine (PAH) homo- or copolymer, optionally comprising modifier units;
(ii) a polyethyleneimine (PEI);
(iii) a polyvinylamine homo- or copolymer, optionally comprising modifier units;
(iv) a poly(vinylbenzyl-tri-$C_1$-$C_4$-alkylammonium salt), for, example a poly(vinylbenzyl-tri-methyl ammoniumchloride);
(v) a polymer of an aliphatic or araliphatic dihalide and an aliphatic N,N,N',N'-tetra-$C_1$-$C_4$-alkyl-alkylenediamine, for example a polymer of (a) propylene-1,3-dichloride or -dibromide or p-xylylene dichloride or dibromide and (b) N,N,N',N'-tetramethyl-1,4-tetramethylene diamine;
(vi) a poly(vinylpyridine) or poly(vinylpyridinium salt) homo- or copolymer;
(vii) a poly(N,N-diallyl-N,N-di-$C_1$-$C_4$-alkyl-ammoniumhalide);
(viii) a homo- or copolymer of a quaternized di-$C_1$-$C_4$-alkyl-aminoethyl acrylate or methacrylate, for example a poly (2-hydroxy-3-methacryloylpropyltri-$C_1$-$C_2$-alkylammonium salt) homopolymer such as a poly(2-hydroxy-3-methacryloylpropyltri-methylammonium chloride), or a quaternized poly(2-dimethylaminoethyl methacrylate or a quaternized poly(vinylpyrrolidone-co-2-dimethylaminoethyl methacrylate);
(ix) polyquat; or
(x) a polyaminoamide (PAMAM), for example a linear PAMAM or a PAMAM dendrimer such as an amino-terminated Starbust™ PAMAM dendrimer (Aldrich).

The above mentioned polymers comprise in each case the free amine, a suitable salt thereof, for example a biomedically acceptable salt or in particular an ophthalmically acceptable salt thereof, as well as any quaternized form, if not specified otherwise.

Suitable comonomers optionally incorporated in the polymers according to (i), (iii), (vi) or (viii) above are, for example, hydrophilic monomers such as acrylamide, methacrylamide, N,N-dimethyl acrylamide, N-vinylpyrrolidone and the like.

Examples of polycationic biopolymers or modified biopolymers that may be employed in the bilayer of the present invention include: basic peptides, proteins or glucoproteins, for example, a poly-c-lysine, albumin or collagen, aminoalkylated polysaccharides such as a chitosan or aminodextranes.

Particular polycationic polymers for forming the bilayer of the present invention include a polyallylamine homopolymer; a polyallylamine comprising modifier units of the above formula (II); a polyvinylamine homo- or -copolymer or a polyethyleneimine homopolymer, in particular a polyallylamine or polyethyleneimine homopolymer, or a poly(vinylamine-co-acrylamid) copolymer.

The foregoing lists are intended to be exemplary, but clearly are not exhaustive. A person skilled in the art, given the disclosure and teaching herein, would be able to select a number of other useful polyionic materials.

It has been discovered previously and disclosed in U.S. application Ser. No. 10/654,566 filed Sep. 3, 2003 (herein incorporated by reference in its entirety) that one layer of a charged polymeric material and one layer of a non-charged polymeric material, which can be non-covalently bonded to the charged polymeric material, can be alternatively deposited onto a substrate to form a biocompatible LbL coating. The non-charged polymeric material according to the invention can be: a homopolymer of a vinyl lactam; a copolymer of at least one vinyl lactam in the presence or in the absence of one or more hydrophilic vinylic comonomers; or mixtures thereof.

The vinyl lactam has a structure of formula (I)

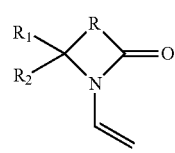

(I)

wherein R is an alkylene di-radical having from 2 to 8 carbon atoms; $R_1$ is hydrogen, alkyl, aryl, aralkyl or alkaryl, preferably hydrogen or lower alkyl having up to 7 and, more preferably, up to 4 carbon atoms, such as, for example, methyl, ethyl or propyl; aryl having up to 10 carbon atoms, and also aralkyl or alkaryl having up to 14 carbon atoms; and $R_2$ is hydrogen or lower alkyl having up to 7 and, more preferably, up to 4 carbon atoms, such as, for example, methyl, ethyl or propyl.

A medical device having an LbL coating thereon can be prepared by applying layers of polyionic materials and optionally noncharged polymeric materials onto a preformed medical device according to any known suitable polyelectrolyte deposition techniques.

Application of an LbL coating may be accomplished in a number of ways as described in pending U.S. patent applications (application Ser. Nos. 09/005,317, 09/774,942, 09/775,104), herein incorporated by reference in their entireties. It has been discovered and disclosed in U.S. application Ser. No. 09/005,317 that complex and time-consuming pretreatment of a core material (medical device) is not required prior to binding of a polyionic material to the core material. By simply contacting a core material of a medical device, for example, a contact lens, with one or more solutions each containing one or more polyionic materials, an LbL coating can be formed on a medical device.

Contacting of a preformed medical device with a coating solution can occur by dipping it into the coating solution or by spraying it with the coating solution. One coating process embodiment involves solely dip-coating and optionally dip-rinsing steps. Another coating process embodiment involves solely spray-coating and spray-rinsing steps. However, a number of alternatives involve various combinations of spray- and dip-coating and rinsing steps may be designed by a person having ordinary skill in the art.

For example, a solely dip-coating process involves the steps of: (a) immersing a medical device in a first coating solution of a first polyionic material; (b) optionally rinsing the medical device by immersing the medical device in a first rinsing solution; (c) immersing said medical device in a second coating solution of a second polyionic material to form a first polyelectrolyte bilayer of the first and second polyionic materials, wherein the second polyionic material has charges opposite of the charges of the first polyionic material; (d) optionally rinsing said medical device by immersing the medical device in the rinsing solution; and (e) optionally repeating steps (a) to (d) for a number of times to form additional polyelectrolyte bilayers. A thicker LbL coating can be produced by repeating steps (a) to (d) preferably for 2 to 40 times. A preferred number of bilayers is about 5 to about 20 bilayers. While more than 20 bilayers are possible, it has been found that delamination may occur in some LbL coatings having an excessive number of bilayers.

The immersion time for each of the coating and rinsing steps may vary depending on a number of factors. Preferably, immersion of the core material into the polyionic solution occurs over a period of about 1 to 30 minutes, more preferably about 2 to 20 minutes, and most preferably about 1 to 5 minutes. Rinsing may be accomplished in one step, but a plurality of rinsing steps can be quite efficient.

Another embodiment of the coating process is a single dip-coating process as described in U.S. application Ser. No. 09/775,104, herein incorporated by reference in its entirety. Such single dip-coating process involves dipping a core material of a medical device in a solution containing a negatively charged polyionic material and a positively charged polyionic material in an amount such that the molar charge ratio of said solution is from about 3:1 to about 100:1. Multiple bilayers can be formed on a medical device by using this single dip-coating process.

Another embodiment of the coating process involves a series of spray coating techniques. For example, a solely spray-coating process generally includes the steps of: (a) spraying a medical device with a first coating solution of a first polyionic material; (b) optionally rinsing the medical device by spraying it with a rinsing solution; (c) spraying said medical device with a second coating solution of a second polyionic material to form a first polyelectrolyte bilayer of the first and second polyionic materials, wherein the second polyionic material has charges opposite of the charges of the first polyionic material; (d) optionally rinsing said medical device by spraying it with the rinsing solution; (e) optionally repeating steps (a) to (d) for a number of times. A thicker LbL coating can be produced by repeating steps (a) to (d) preferably for 2 to 40 times.

The spray coating application may be accomplished via a process selected from the group consisting of an air-assisted atomization and dispensing process, an ultrasonic-assisted atomization and dispensing process, a piezoelectric assisted atomization and dispensing process, an electro-mechanical jet printing process, a piezo-electric jet printing process, a piezo-electric with hydrostatic pressure jet printing process, and a thermal jet printing process;

and a computer system capable of controlling the positioning of the dispensing head of the spraying device on the ophthalmic lens and dispensing the coating liquid. Those spraying coating processes are described in U.S. Application No. 60/312199, herein incorporated by reference in its entirety. By using such spraying coating processes, an asymmetrical coating can be applied to a medical device. For example, the back surface of a contact lens can be coated with a hydrophilic and/or lubricous coating material and the front surface of the contact lens can be coated with an antimicrobial metal-containing LbL coating. It is also possible to produce a coating on a contact lens, the coating having a functional pattern so as to provide simultaneously multiple benefits to a wearer.

In accordance with the present invention, polyionic material solutions can be prepared in a variety of ways. In particular, a polyionic solution of the present invention can be formed by dissolving the polyionic material(s) in water or any other solvent capable of dissolving the materials. When a solvent is used, any solvent that can allow the components within the solution to remain stable in water is suitable. For example, an alcohol-based solvent can be used. Suitable alcohols can include, but are not limited to, isopropyl alcohol, hexanol, ethanol, etc. It should be understood that other solvents commonly used in the art can also be suitably used in the present invention.

Whether dissolved in water or in a solvent, the concentration of a polyionic material in a solution of the present invention can generally vary depending on the particular materials being utilized, the desired coating thickness, and a number of other factors. However, it may be typical to formulate a relatively dilute aqueous solution of polyionic material. For example, a polyionic material concentration can be between about 0.001% to about 0.25% by weight, between about 0.005% to about 0.10% by weight, or between about 0.01% to about 0.05% by weight.

In general, the polyionic solutions mentioned above can be prepared by any method well known in the art for preparing solutions. For example, in one embodiment, a polyanionic solution can be prepared by dissolving a suitable amount of the polyanionic material, such as polyacrylic acid having a molecular weight of about 90,000, in water such that a solution having a certain concentration is formed. In one embodiment, the resulting solution is a 0.001 M PAA solution. Once dissolved, the pH of the polyanionic solution can also be adjusted by adding a basic or acidic material. In the embodiment above, for example, a suitable amount of 1 N hydrochloric acid (HCl) can be added to adjust the pH to 2.5.

However, where a coating solution containing a first polyionic material is used to form an innermost layer of a biocompatible LbL coating of the invention on the surface of a medical device, it is desirable that the concentration of the first charged polymeric material in the solution is sufficiently high enough to increase the hydrophilicity of the LbL coating. Preferably, the concentration of the charged polymeric material in a solution for forming the innermost layer of an LbL coating is at least three folder higher than the concentration of a coating material in a coating solution for forming subsequent layers of the LbL coating. More preferably, the concentration of the charged polymeric material in a solution for forming the innermost layer of an LbL coating is at least ten folder higher than the concentration of a coating material in a coating solution for forming subsequent layers of the LbL coating.

Polycationic solutions can also be formed in a manner as described above. For example, in one embodiment, poly(allylamine hydrochloride) having a molecular weight of about 50,000 to about 65,000 can be dissolved in water to form a 0.001 M PAH solution. Thereafter, the pH can also be adjusted to 2.5 by adding a suitable amount of hydrochloric acid.

In some embodiments of the present invention, it may be desirable to use a solution containing both polyanionic and polycationic materials within a single solution. For example, a polyanionic solution can be formed as described above, and then mixed with a polycationic solution that is also formed as described above. In one embodiment, the solutions can then be mixed slowly to form the coating solution. The amount of each solution applied to the mix depends on the molar charge ratio desired. For example, if a 10:1 (polyanion:polycation) solution is desired, 1 part (by volume) of the PAH solution can be mixed into 10 parts of the PAA solution. After mixing, the solution can also be filtered if desired.

In order to alter various characteristics of the coating, such as thickness, the molecular weight of the polyionic materials including polyquats can be varied. In particular, as the molecular weight is increased, the coating thickness generally increases. However, if the increase in molecular weight increase is too substantial, the difficulty in handling may also increase. As such, polyionic materials used in a process of the present invention will typically have a molecular weight $M_n$ of about 2,000 to about 150,000. In some embodiments, the molecular weight is about 5,000 to about 100,000, and in other embodiments, from about 75,000 to about 100,000.

In addition to polyionic and non-charged polymeric materials, a coating solution for forming the bilayer or part of it, can also contain additives. As used herein, an additive can generally include any chemical or material. For example, active agents, such as antimicrobials and/or antibacterials can be added to a solution forming the bilayer, particularly when used in biomedical applications. Some antimicrobial polyionic materials include polyquaternary ammonium compounds, such as those described in U.S. Pat. No. 3,931,319 to Green et al. (e.g. POLYQUAD®).

Moreover, other examples of materials that can be added to a coating solution are polyionic materials useful for ophthalmic lenses, such as materials having radiation absorbing properties. Such materials can include, for example, visibility-tinting agents, iris color modifying dyes, and ultraviolet (UV) light tinting dyes.

Still another example of a material that can be added to a coating solution is a polyionic material that inhibits or induces cell growth. Cell growth inhibitors can be useful in devices that are exposed to human tissue for an extended time with an ultimate intention to remove (e.g. catheters or Intra Ocular Lenses (IOLs), where cell overgrowth is undesirable), while cell growth-inducing polyionic materials can be useful in permanent implant devices (e.g. artificial cornea).

When additives are applied to a coating solution, such additives, preferably, have a charge. By having a positive or negative charge, the additive can be substituted for the polyionic material in solution at the same molar ratio. For example, polyquaternary ammonium compounds typically have a positive charge. As such, these compounds can be substituted into a solution of the present invention for the polycationic component such that the additive is applied to the core material of an article in a manner similar to how a polycationic would be applied.

A preferred number of bilayers in an LbL coating are about 5 to about 20 bilayers. While more than 20 bilayers are possible, it has been found that delamination may occur in some LbL coating having excessive number of bilayers.

An LbL coating can be formed from at least one polyionic material, preferably two polyionic materials having charges opposite to each other.

An LbL coating preferably comprises at least one layer of a lubricious coating material which is selected from the group consisting of PAMAM dendrimers, PAAm-co-PAA, PVP-co-PAA, glycosaminoglycanes, fucoidan, poly-aspartic acid, poly-glutamic acid, carboxymethyl cellulose, carboxymethyl dextrans, alginates, pectins, gellan, carboxyalkyl chitins, carboxymethyl chitosans, sulfated polysaccharides, glucoproteins, and aminoalkylated polysaccharides.

Exemplary negatively charged polyionic materials having —COOH groups include, without limitation, a linear or branched polyacrylic acid (PAA), polymethacrylic acid (PMA), a polyacylic acid or polymethacrylic acid copolymer, a carboxy-terminated polymer of a diamine and a di- or poly-carboxylic acid (e.g., carboxy-terminated Starburst™ PAMAM dendrimers from Aldrich), and a maleic or fumaric acid copolymer.

It is believed that silver ions are incorporated into the polyelectrolyte LbL coating via ion exchange mechanism to replace $H^+$ in the —COOH groups.

Silver ions can be reduced to silver or silver nano-particles either by means of a reducing agent or by means of heating (e.g., autoclave) or by UV irradiation. During the manufacturing of medical devices, for example, contact lenses, autoclave can be used to sterilize the medical devices while reducing silver ions into silver nano-particles.

A medical device of the invention can also be made by first applying an LbL coating (described above) to a mold for making a medical device and then transfer-grafting the LbL coating to the medical device made from the mold, in substantial accordance with the teachings of U.S. patent application (Ser. No. 09/774,942), herein incorporated by reference in its entirety.

Methods of forming mold sections for cast-molding a contact lens are generally well known to those of ordinary skill in the art. The process of the present invention is not limited to any particular method of forming a mold. In fact, any method of forming a mold can be used in the present invention. However, for illustrative purposes, the following discussion has been provided as one embodiment of forming a contact lens mold on which an LbL coating can be formed in accordance with the present invention.

In general, a mold comprises at least two mold sections (or portions) or mold halves, i.e. first and second mold halves. The first mold half defines a first optical surface and the second mold half defines a second optical surface. The first and second mold halves are configured to receive each other such that a contact lens forming cavity is formed between the first optical surface and the second optical surface. The first and second mold halves can be formed through various techniques, such as injection molding. These half sections can later be joined together such that a contact lens-forming cavity is formed therebetween. Thereafter, a contact lens can be formed within the contact lens-forming cavity using various processing techniques, such as ultraviolet curing.

Examples of suitable processes for forming the mold halves are disclosed in U.S. Pat. No. 4,444,711 to Schad; U.S. Pat. No. 4,460,534 to Boehm et al.; U.S. Pat. No. 5,843,346 to Morrill; and U.S Pat. No. 5,894,002 to Boneberger et al., which are also incorporated herein by reference.

Virtually all materials known in the art for making molds can be used to make molds for making contact lenses. For example, polymeric materials, such as polyethylene, polypropylene, and PMMA can be used. Other materials that allow UV light transmission could be used, such as quartz glass.

Once a mold is formed, a transferable LbL coating (described above) can be applied onto the optical surface (inner surface) of one or both mold portions by using the above-described LbL deposition techniques. The inner surface of a mold portion is the cavity-forming surface of the mold and in direct contact with lens-forming material. A transferable LbL coating can be applied onto the mold portion defining the posterior (concave) surface of a contact lens or on the mold section defining the anterior surface of a contact lens or on both mold portions.

Once a transferable LbL coating is applied onto the optical surface of one or both mold portions, a lens material can then be dispensed into the contact lens forming cavity defined by the assembled mold halves. In general, a lens material can be made from any polymerizable composition. In particular, when forming a contact lens, the lens material may be an oxygen-permeable material, such as fluorine- or siloxane-containing polymer. For example, some examples of suitable substrate materials include, but are not limited to, the polymeric materials disclosed in U.S. Pat. No. 5,760,100 to Nicolson et al., which is incorporated herein by reference. The lens material can then be cured, i.e. polymerized, within the contact lens-forming cavity to form the contact lens, whereby at least a portion of the transferable coating detaches from the optical surface and reattaches to the formed contact lens.

Thermal curing or photo curing methods can be used to curing a polymerizable composition in a mold to form an ophthalmic lens. Such curing methods are well-known to a person skilled in the art.

The invention, in another aspect, provides a method for forming an antimicrobial metal-containing LbL coating on a medical device. The method comprises alternatively applying, in no particular order, at least one layer of a negatively charged polyionic material having —COOAg groups and at least one layer of a positively charged polyionic material onto a medical device to form the antimicrobial metal-containing LbL coating.

The step of applying can be achieved according to any methods, preferably described above. A negatively charged polyionic material having —COOAg groups can be prepared according to any known methods. For example, a negatively charged polyionic material having —COOAg groups can be prepared by adding a soluble silver salt into a solution of a negatively charged polyionic material having —COOH groups. Exemplary negatively charged polyionic materials having —COOH groups have been described above. Exemplary silver salts include, without limitation, silver nitrate, silver acetate, silver citrate, silver sulfate, silver lactate, and silver halide.

In a preferred embodiment, $Ag^+$ in the antimicrobial metal-containing LbL coating on a medical device of the invention can be further reduced to silver or silver nano-particles either by means of a reducing agent or by means of heating (e.g., autoclave) or by UV irradiation.

The invention, in a further aspect, provides a medical device having a core material and an antimicrobial metal-containing layer-by-layer (LbL) coating that is not covalently attached to the medical device and can impart to the medical device an increased hydrophilicity, wherein the antimicrobial metal-containing LbL coating comprises at least one layer of a negatively charged polyionic material having —COOAg groups and/or silver nanoparticles formed by reducing $Ag^+$ ions associated with the —$COO^-$ groups of the negatively charged polyionic material.

The increased hydrophilicity is preferably characterized by having an averaged contact angle of 80 degrees or less.

In a preferred embodiment, the antimicrobial LbL coating of the invention formed on a medical device comprises at least one layer of a negatively charged polyionic material having —COOAg groups.

In another preferred embodiment, the antimicrobial LbL coating of the invention formed on a medical device comprises silver nanoparticles formed by reducing $Ag^+$ ions associated with the $—COO^-$ groups of the negatively charged polyionic material which is one of coating materials used in preparing an antimicrobial metal-containing LbL coating. The antimicrobial metal-containing LbL coating can be formed by applying at least one layer of a negatively charged polyionic material having —COOAg groups and at least one layer of a positively charged polyionic materials onto the medical device. Alternatively, the antimicrobial metal-containing LbL coating can be formed by: dipping a medical device having an LbL coating comprising at least one layer of a negatively charged polyionic material with —COOH groups, into a solution containing silver ions for a period of time sufficient to replace a desired amount of $H^+$ with silver ions; and then reducing silver ions contained in the LbL coating to form silver nano-particles by means of a reducing agent, UV irradiation or heating.

In accordance with the invention, the above-described antimicrobial LbL coating of the invention comprises preferably at least one capping layer of a polyionic material, more preferably at least one capping bilayer of two oppositely charged polyionic materials or at least one capping layer of a charged polymeric material and a non-charged polymeric material that can be non-covalently bonded to the charged polymeric material, on top of the outmost antimicrobial metal-containing layer. One or more capping layers or bilayers can be served as a diffusion barrier to control the diffusion of silver or other antimicrobial metal ions out of the antimicrobial LbL coating.

An antimicrobial metal-containing LbL coating of the present invention may find particular use in extended-wear contact lenses. The LbL coating of the invention may have a minimal adverse effects on the desirable bulk properties of the lens, such as oxygen permeability, ion permeability, and optical properties. Moreover, the out diffusion of silver or other antimicrobial metals from the antimicrobial metal-containing LbL coating of the present invention is believed to be minimized. It is surprised to find that although an antimicrobial LbL coating of the invention contains silver nano-particles instead of silver ions, it still imparts to a medical device a desired level of antimicrobial activity.

A medical device having a core material and an antimicrobial metal-containing LbL coating preferably can have an increased surface hydrophilicity and exhibit at least 50% inhibition of viable microorganisms. Preferably, the increased hydrophilicity is characterized by having an averaged contact angle of about 80 degrees or less.

The previous disclosure will enable one having ordinary skill in the art to practice the invention. In order to better enable the reader to understand specific embodiments and the advantages thereof, reference to the following examples is suggested.

EXAMPLE 1

Contact angle

The contact angle generally measures the surface hydrophilicity of a medical device, e.g., a contact lens. In particular, a low contact angle corresponds to more hydrophilic surface. Average contact angles (Sessile Drop) of contact lenses are measured using a VCA 2500 XE contact angle measurement device from AST, Inc., located in Boston, Mass.

Antimicrobial Activity Assay

Antimicrobial activity of a contact lens with or without a silver-containing antimicrobial LbL coating of the invention is assayed against *Pseudomonas aeruginosa* GSU # 3, which is isolated from a corneal ulcer. Bacterial cells of *Pseudomnas aeruginosa* GSU # 3 stored in a lyophilized state. Bacteria are grown on an tryptic soy agar slant for 18 hours at 37° C. The cells are harvested by centrifugation and washed twice with sterile, Delbeco's phosphate buffered saline. Bacterial cells are suspended in PBS and adjusted to Optical Density of $10^8$ cfu. The cell suspension is serially diluted to $10^3$ cfu/ml.

Lenses having a silver-containing antimicrobial LbL coating are tested against the control lenses (i.e., without a silver-containing antimicrobial LbL coating of the invention). 200 µl of from about $5 \times 10^3$ to $1 \times 10^4$ cfu/ml of P. aeruginosa GSU #3 is placed on the surface of each lens. Incubate at 25° C. for 24 hours. Aspirate 50 µl out of the lens, serially dilute and plate out on agar plates to determine the microbial load of each lens. At 24 hours, colony counts are taken.

EXAMPLE 2

Chemicals
Silver acetate (M.W. 166.9) is purchased from Aldrich (product number 21,667-4).
Dimethylamine borane (DMAB) (M.W 58.92) is used as a reducing agent for reducing silver ions to silver nanoparticles and purchased from Aldrich (product number 18,023-8).
PAA (polyacrylic acid) with Mw~90,000 (25% solution) is from Polyscience.
PAAm (polyacrylamide) with Mw~5,000,000 (1% solution) is from Polyscience.
PAH (polyallylarnine hydrochloride) with Mw~70,000 is from Aldrich.
PAAm-co-PAANa (arnide:acid =30:70, Mw~200,000, solid), an anionic acrylamide polymer is from Polysciences.
PAAm-co-PMAB (amide:amine=80:20, Mw~50,000, 20% solution), a cationic acrylamide polymer, is from Polysciences.
Solutions
Silver solution: The silver solution was prepared by dissolving a suitable amount of silver acetate (0.1669 g/200 ml) in water to form a 5 mM silver acetate solution.
DMAB solution: The DMAB solution was prepared by dissolving a suitable amount of DMAB (0.05892g/1 L) to form a 1 mM DMAB solution.
Solution S1: PAH, about $10^{-2}$ M (0.935 g/litter), pH 3.0
Solution S2: PAA, about $10^{-2}$ M (2.88g/litter), pH 3.0
Solution S3: PAAm, about $10^{-2}$M (71 g/litter), pH 3.0
Solution S4: PAA, ca. $10^{-2}$ M (2.88g/litter), pH 2.0 for pre-coating
Solution S5: PAAm-co-PMAB (cationic), ca. $10^{-2}$M (1.0438 g/litter), pH 3.0
Solution S6: PAAm-co-PAANa, ~$10^{-2}$M (0.72 g/litter), pH 3.0
Solution S7: PAH, ~$10^{-2}$ M (0.935 g/litter)), pH 3.0
Coatings
Group A (polystyrene slides): 21 dips (15 minutes each dip) with water rinse between dips, S1/S2/S3/S2/S3/S2/S3/S2/S3/S2/S3/S2/S3/S2/S3/S2/S3/S2/S3.
Group B (polystyrene slides): 22 dips (15 minutes each dip) with water rinse between dips: S7/S4/S5/S6/S5/S6/S5/S6/S5/S6/S5/S6/S5/S6/S5/S6/S5/S6/S5/S6/S5/S6.

Group C (contact lenses, lotrafilcon B): 11 dips (5 minutes each dip) with water rinse between dips: S4/S5/S6/S5/S6/S5/S6/S5/S6/S5/S6.

Description of Samples

Group A.

A1: 1 hr in silver acetate bath, 30 minute rinse, 10 min. in DMAB reduction bath
A2: 1 hr in silver acetate bath, 5 minute rinse, 2 min. in DMAB reduction bath
A3: 35 minutes dip in silver acetate bath, 5 minute rinse, 2 min. in DMAB reduction bath
A4: 1 hr in silver acetate bath, 5 minute rinse, 2 min. in DMAB reduction bath repeated this process 5 times (5 cycle loading)
A5: 1 hr in silver acetate bath, 5 minute rinse, no reduction
A6: control, no silver. Film as deposited and thermal-stabilized Group B.

B1: 10 min. in silver acetate bath, 5 minute rinse, 10 min. in DMAB reduction bath
B2: 20 min. in silver acetate bath, 5 minute rinse, 2 min. in DMAB reduction bath
B3: 30 min. in silver acetate bath, 5 minute rinse, 2 min. in DMAB reduction bath
B4: 5 min. in silver acetate bath, 5 minute rinse, 2 min. in DMAB reduction bath
B5: 60 min. in silver acetate bath, 5 minute rinse, 2 min. in DMAB reduction bath
B6: 10 min. in silver acetate bath, 5 minute rinse, no reduction
B7: control, no silver. Film as deposited and thermal-stabilized Group C. (contact lenses)

C1: 5 min. in silver acetate bath, 5 minute rinse, 2 min. in DMAB reduction bath
C2: 10 min. in silver acetate bath, 5 minute rinse, 10 min. in DMAB reduction bath
C3: 20 min. in silver acetate bath, 5 minute rinse, 2 min. in DMAB reduction bath
C4: 30 min. in silver acetate bath, 5 minute rinse, 2 min. in DIMAB reduction bath
C5: 60 min. in silver acetate bath, 5 minute rinse, 2 min. in DMAB reduction bath
C06: 10 min. in silver acetate bath, 5 minute rinse, no reduction
C07: control, no silver. Film as deposited and thermal-stabilized Antimicrobial activity of Samples A1 to A5 is assayed against *Pseudomonas aeruginosa* GSU # 3 according to the procedure described in Example 1. All samples show excellent antimicrobial activity (characterized by at least a 3-log reduction, i.e. 99.9% inhibition) of viable cells as compared to the control.

EXAMPLE 3

Polyacrylic acid (PAA) solution: A solution of polyacrylic acid having a molecular weight of about 90,000, from PolyScience, is prepared by dissolving a suitable amount of the material in water to form a 0.001 M PAA solution. The PAA concentration is calculated based on the repeating unit in PAA. Once dissolved, the pH of the polyanionic PAA solution is adjusted by adding 1 N nitric acid until the pH is about 2.5.

Poly(ethyleneimine) (PEI) solution: A solution of PEI having a molecular weight of about 70,000 from Polyscience, is prepared by dissolving a suitable amount of the material in water to form a 0.001M PEI solution. The PEI concentration is based on the repeating unit in PEI. The pH of the PEI solution is adjusted by adding 0.1 M nitric acid until the pH is about 8.0.

Polyacrylic acid-silver (PAA-Ag) solution: A PAA-Ag solution is prepared by dissolving a suitable amount of PAA (molecular weight of 90,000, from PolyScience) and silver nitrate ($AgNO_3$) in water to form a 0.01 M of PAA and 0.01 M of $AgNO_3$. The PAA concentration is calculated based on the repeating unit in PAA. Once dissolved, the pH of the PAA-Ag solution is adjusted by adding 1 N nitric acid until the pH is about 2.5.

Sodium borohydride ($NaBH_4$) solution: a solution of $NaBH_4$ solution is prepared by dissolving a suitable amount of sodium borohydride solid (from Aldrich) in water to form 0.001 M $NaBH_4$ solution.

A coating having multiple bilayers of PAA-Ag/PEI is formed on a silicone wafer and a soft contact lens made of a fluorosiloxane hydrogel material, lotrafilcon A (CIBA Vision). The contact lens (and also the silicone wafer) is dipped in four PAA solutions (0.001 M, pH 2.5) for 5 min each and a total of 20 minutes to form a first layer on the lens. The lens with a first layer of PAA is then dipped in the PAA-Ag solution for 5 minutes and then dipped in the PEI solution for 5 minutes. Then the steps of dipping in the PAA-Ag solution for 5 minutes followed by dipping in the PEI solution for 5 minutes are repeated for a desired number of times to build up a desired number of bilayers of PAA-Ag/PEI on the lens (or silicon wafer). Finally, the lens is dipped in $NaBH_4$ solution for 5 min. There is rinsing step involved in the above coating process. All the lenses are then released and autoclaved in water or in PBS.

The coating thickness on silicone wafer is about 21 nm as measured by ellipsometry. As listed in Table 1, the coated lenses are hydrophilic with contact angles of about 30-65 degrees, as compared to the uncoated lenses with a contact angle of about 110 degrees. All lenses passed Sudan black staining test.

TABLE 1

| Autoclave medium | water | PBS |
| --- | --- | --- |
| Contact angle* | 29 | 65 |
| Bacterial Inhibition[#] | 99.9% | 97.5% |

*Average contact angle from 3 lenses
[#]Averaged CFU/lens for control lenses is about $1.0 \times 10^4$.

Antimicrobial activity of a contact lens with a silver-containing antimicrobial LbL coating of the invention was assayed against *Pseudomonas aeruginosa* GSU #3 according to the procedure described in Example 1. The control lenses were Lotrafilcon A contact lenses without a silver-containing antimicrobial LbL coating. All lenses with an antimicrobial LbL coating of the invention, which are autoclaved in either water or PBS, show antimicrobial activity, characterized by a 97.5% to 99.9% inhibition of viable cells as compared to the control lenses (Table 1).

Although various embodiments of the invention have been described using specific terms, devices, and methods, such description is for illustrative purposes only. The words used are words of description rather than of limitation. It is to be understood that changes and variations may be made by those skilled in the art without departing from the spirit or scope of the present invention, which is set forth in the following claims. In addition, it should be understood that aspects of the various embodiments may be interchanged either in whole or in part. Therefore, the spirit and scope of the appended claims should not be limited to the description of the preferred versions contained therein.

What is claimed is:

1. A method for preparing a medical device with an antimicrobial metal-containing LbL coating thereon, comprising the steps of: (a) alternatively applying, in no particular order, at least one layer of a negatively charged polyionic material having —COOAg groups and at least one layer of a positively charged polyionic material onto the medical device to form the polyelectrolyte LbL coating (b) autoclaving the medical device of step (a) to reduce the silver ions contained in the polyelectrolyte LbL coating to form silver nano-particles wherein the medical device having the silver nano-particle-containing antimicrobial LbL coating exhibits at least 50% inhibition of viable microorganisms.

2. A method for preparing a medical device with an antimicrobial metal-containing LbL coating thereon, comprising the steps of:

(a) obtaining a mold for making the medical device, wherein the mold comprises a first mold portion defining a first optical surface and a second mold portion defining a second optical surface, wherein said first mold portion and said second mold portion are configured to receive each other such that a medical device-forming cavity is formed between said first optical surface and said second optical surface;

(b) applying a transferable LbL coating, using a layer-by-layer polyelectrolyte deposition technique, onto at least one of said optical surfaces, wherein the transferable LbL coating comprises one or more bilayers of a negatively charged polyionic material having —COOAg groups and a positively charged polyionic material;

(c) positioning said first mold portion and said second mold portion such that said mold portions receive each other and said optical surfaces define said medical device forming cavity;

(d) dispensing a polymerizable composition into said medical device-forming cavity; and (e) curing said polymerizable composition within said medical device-forming cavity such that the medical device is formed, whereby said transferable LbL coating detaches from said at least one optical surface of said mold portion and reattaches to said formed medical device such that said medical device becomes coated with the antimicrobial metal-containing LbL coating;

(f) autoclaving the medical device with the antimicrobial metal-containing LbL coating of step (e) to reduce the silver ions contained in the polyelectrolyte LbL coating to form silver nano-particles wherein the medical device having the silver nano-particle-containing antimicrobial LbL coating exhibits at least 50% inhibition of viable microorganisms.

* * * * *